United States Patent [19]

Yolles

[11] 4,419,340

[45] * Dec. 6, 1983

[54] CONTROLLED RELEASE OF ANTICANCER AGENTS FROM BIODEGRADABLE POLYMERS

[75] Inventor: Seymour Yolles, Newark, Del.

[73] Assignee: University of Delaware, Newark, Del.

[*] Notice: The portion of the term of this patent subsequent to Jun. 3, 1992 has been disclaimed.

[21] Appl. No.: 208,506

[22] Filed: Nov. 20, 1980

Related U.S. Application Data

[63] Continuation of Ser. No. 859,766, Dec. 12, 1977, abandoned, which is a continuation-in-part of Ser. No. 504,588, Sep. 9, 1974, abandoned, which is a continuation of Ser. No. 102,431, Dec. 29, 1970, Pat. No. 3,887,669, which is a continuation-in-part of Ser. No. 809,946, Mar. 24, 1969, abandoned.

[51] Int. Cl.³ .................. A61K 9/26; A61K 31/74; A61K 47/00
[52] U.S. Cl. ........................ 424/19; 424/22; 424/78
[58] Field of Search .................. 424/19–22, 424/78; 128/260

[56] References Cited

U.S. PATENT DOCUMENTS

| | | | |
|---|---|---|---|
| 3,773,919 | 11/1973 | Boswell et al. | 424/19 |
| 3,887,699 | 6/1975 | Yolles | 424/19 |
| 3,904,663 | 9/1975 | Tobe et al. | 424/287 |
| 3,976,071 | 8/1976 | Sadek | 128/260 |
| 3,991,766 | 11/1976 | Schmitt et al. | 128/335.5 |

OTHER PUBLICATIONS

Merck Index 9th Ed. (1976) Merck & Co. Rahway, N.J., p. 359 Entry 2751 Cyclophosphamide, Antineoplastic; Antineoplastic p. 456 Entry 3428 Doxorubicin (U.S. 3590 028 (1971) Farmitalia).

Yolles et al., J. Pharm. Sci. 64(1): 115–116 Jan. 1975 "Timed Release Depot for Anticancer Agents".

Yolles et al., Acta Pharmaceuitca Suecica 15(5): 382–388 (1978), "Timed-Release Depot for Anticancer Agents II."

Yolles et al., Parenteral Drug Assn. Jl. 32(4): 188–191 (1978), Timed Release Depot for Anticancer Drugs: "Release of Drugs Covalently Bonded to Polymers".

*Primary Examiner*—Shep K. Rose
*Attorney, Agent, or Firm*—Connolly and Hutz

[57] ABSTRACT

Polymeric articles for controllably dispensing anticancer agents are disclosed which are formed from biodegradable polymeric materials containing the agents.

3 Claims, No Drawings

CONTROLLED RELEASE OF ANTICANCER AGENTS FROM BIODEGRADABLE POLYMERS

CROSS REFERENCE TO RELATED APPLICATIONS

This application is a continuation of Ser. No. 859,766, filed Dec. 12, 1977, now abandoned, which is a continuation-in-part of Ser. No. 504,588, filed Sept. 9, 1974, now abandoned, which is a continuation of Ser. No. 102,431, filed Dec. 29, 1970, now U.S. Pat. No. 3,887,699, which is in turn a continuation-in-part of Ser. No. 809,946, filed Mar. 24, 1969, now abandoned.

BACKGROUND OF THE INVENTION

1. Field of the Invention

This invention relates broadly to the controlled release of drugs to the bloodstream and tissues of mammals and more particularly to a shaped article formed from a biodegradable polymer which contains one or more anticancer agents so that the article is suitable for implantation in a mammal to controllably release the anticancer agents.

2. Description of the Prior Art

Medical science has long recognized the need for methods to controllably release therapeutic agents and other drugs to the bodies of patients. Recently, a great deal of research has been initiated in attempting to find new release systems to fulfill this need. Several such systems have been recommended.

One common method for obtaining controlled release is to envelop the active substance with coatings which are attacked by digestive juices in the stomach. This technique has been widely used recently for time-release analgesics. There are some problems with this method, however, such as: (1) it is difficult to obtain the proper distribution of coating thicknesses to give the desired release; and (2) the sojourn time of the coated agent in the digestive tract is relatively short, thereby making this unsuitable for long-term release.

Another method of obtaining controlled release is to mix the active substance with various binders such as fats, waxes, and natural or synthetic polymers to slow down release. Many of the binders, however, are unsuitable for use with many drugs. Furthermore, these combinations of binders and drugs tend to disperse quickly after they enter the body due to the binder's solubility in body fluids, the washing effect of the body fluids and/or the attack of digestive juices. After the binder has been so dispersed, all control over the release of the drug is lost.

Other researchers have even suggested that drugs be chemically modified to affect their release and absorption into the bloodstream. The degree of difficulty of this method for obtaining controlled release is clear.

More recently, the possibility of somehow incorporating drugs into polymeric materials to control drug release has been considered. Thus Furuse et al., U.S. Pat. No. 3,514,517, teach that suppositories containing spermicidal agents can be formed by blending the agents with low molecular weight polyethylene glycols; Hill, U.S. Pat. No. 3,458,622, teaches that tablets for controlling the release of medicinal agents for up to eight hours can be formed from a blend of a polymeric vinyl pyrrolidone with a carboxy vinyl hydrophilic polymer; Weil et al., U.S. Pat. No. 3,469,005, teach that drugs for reducing blood pressure in mammals can be incorporated into solid vehicles such as lactose, corn-starch, microcrystalline cellulose, talc, stearic acid, magnesium stearate, gums, etc.; Merabi et al., U.S. Pat. No. 3,495,000, have found that controlled release matrices can be prepared consisting of a dialdehyde starch and ethyl cellulose, polyvinyl chloride or polyvinylpyrrolidone, but that mixtures of the same starches with other pharmaceutically acceptable polymers such as methylcellulose or carboxymethylcellulose do not yield compositions suitable for controlled release; and Herrmann, U.S. Pat. No. 2,155,658, teaches that medical preparations for injection into the body which are flowable above body temperature but solid at body temperature after injection ca be made from polymerized vinyl alcohols and their water soluble derivatives and a solvent for such material.

Another technique for incorporating drugs into polymeric matrices is described in Levesque, U.S. Pat. No. 2,987,445 and in Edicott, U.S. Pat. No. 3,087,860. These patents teach a drug dispenser formed from synthetic polymers containing solid particles of a water-leachable drug. Usually the polymer matrix is shaped in the form of a pill which is intended to be orally ingested. This drug dispenser is limited, however, to water-soluble drugs and has relatively short release times, i.e., typically 8–12 hours.

While the above-mentioned patents describe various mixtures of drugs with polymers, Long et al. have taught another method for constructing a controlled release device from polymers in U.S. Pat. No. 3,279,996. Long et al. form a capsule or container from polysiloxane which is intended for implantation. This device has the advantage of making extended time-release treatment possible, but suffers a disadvantage since the possibility exists that the polysiloxane container will develop pinholes or a rupture resulting in an undesired and potentially harmful large amount of drug being released almost instantaneously.

A polymeric drug dispenser formed from crystalline polymeric materials is disclosed in U.S. Pat. No. 3,880,991, issued on Apr. 29, 1975. The device described therein offers many improvements over existing controlled release devices, but suffers a disadvantage when subcutaneously implanted since the polymers described therein are not biodegradable. Thus, a separate removal step often necessitating minor surgery is required.

Biodegradable polymer matrices have been previously described in my earlier applications, including Ser. Nos. 504,588, filed Dec. 9, 1974; 102,431, filed Dec. 29, 1970; and 809,946, filed Mar. 24, 1969. Additionally, poly(lactic acid) has been disclosed by others for this use in U.S. Pat. No. 3,773,919 issued Dec. 20, 1973. Poly(lactic acid) films have also been shown to release anticancer agents such as cyclophosphamide and cis-dichlorodiammine-platinum(II) in healthy rats. See Yolles, S., Leafe, T. D., and Meyer, F. J., "Timed-Release Depot for Anticancer Agents," *J. Pharm. Sci.*, 64, No. 1, pp. 115-6, Jan. 1975.

SUMMARY OF THE INVENTION

Anticancer agents dispersed in a biodegradable polymeric material can be formed to a solid shape which will exude the agents to the surface of the polymeric article. For purposes of this description, the term exude is used to mean the migration from the interior of the polymer material to its surface until the surface is covered with a layer of the agent and an equilibrium is established between the surface layer and the agent at the interior of the polymeric material. If the surface layer is partially or totally removed, the equilibrium is destroyed and further amounts of the agent permeate to the surface until equilibrium is re-established. This cycle will repeat itself until the supply of agent has been exhausted from the polymeric material. The surface layer can be removed in many ways, including but not limited to: rubbing it off; brushing it off; washing it off; dissolving it off; etc.

Relying upon this discovery, a novel article for dispensing anticancer agents has been invented which comprises:

1. a biodegradable polymeric material formed to a solid shaped article; and,
2. one or more anticancer agents substantially uniformly and intimately dispersed throughout portions of the polymeric article.

This drug dispenser provides an economical and reliable method for automatically dispensing controlled quantities of an anticancer agents over a short or an extended period of time. Such a device can be implanted within a mammal's body so that it will dispense the required amounts of one or more agents continuously over extended periods of time without the patient having to rely on periodic injections or oral ingestion of agents. Once implanted, the dispenser can be forgotten and the patient can rest assured that his body is continuously and automatically receiving the prescribed amount of agent.

A most important advantage of the polymeric dispenser described herein is the degree of flexibility which can be obtained in administration techniques. As stated above, one suitable method for releasing agents from this device to a mammal's body is to subcutaneously implant the device. There are many other methods, however. For example, the device can be extruded into the shape of thin "spaghetti" which can be implanted in a muscle, or into a solid tumor, or the polymeric material can be formed into various sized spheroids or particles for ingestion or injection into a patient. Additionally, the polymeric material can be formed into hollow tubing suitable for catheters. In short, the dispenser of this invention can be formed into limitless solid or hollow shapes each suitable for particular methods of controllably releasing agents to the patient's bloodstream.

As mentioned above, the drug dispenser described herein has the additional advantage of a biodegradable polymeric matrix. It should be clear that this is particularly important when the device is subcutaneously implanted.

The use of a biodegradable polymeric matrix to administer anticancer agents has been found surprisingly efficacious. Initially, as is known, most anticancer drugs are very toxic which limits the dosage which can be administered. Using the matrices described herein, it has been found that doses much larger than those normally toxic can be administered. Moreover, the biodegradable polymer matrix can be designed to release amounts of these agents which are lower than are normally infused by injection. Despite the fact that the release is low, the agents have been found to be extremely efficacious.

DESCRIPTION OF THE PREFERRED EMBODIMENTS

The polymeric materials used to manufacture the instant device must have high melting points so that they won't soften when exposed to fairly high temperatures such as those encountered with human body fluids. Preferably the material will have a melting point of 100° C. or more so that the device can be sterilized at high temperatures.

A further limitation on suitable polymeric materials is that they be biodegradable. The term "biodegradable" is used to mean materials which are attacked and broken down into simpler chemical species by substances found in mammals such as enzymes.

Some naturally occurring polymers such as sugar phosphates are known to be biodegradable.

Synthetic polymers can also be prepared which are biodegradable. Examples include poly(lactic acid) and polyglycolic acid, or their derivatives. These are the preferred biodegradable polymers for use in this invention because they are broken down into innocuous products like carbon dioxide and water and because they are commercially available.

Useful poly(lactic acids) include both homopolymers and copolymers. Usually, these are prepared from the cyclic esters of lactic acids. Both $L(+)$ and $D(-)$ forms of lactic acid may be used to prepare the poly(lactic acid) as well as the optically inactive DL-lactic acid mixture or any desired mixtures of $D(-)$ and $L(+)$ lactic acids.

Lactic acid copolymers offer an important degree of flexibility in choosing the life of a polymer matrix since this can be controlled through the amount and type of comonomer used. Some illustrative examples of suitable comonomers include: glycolide, $\beta$-propiolactone, tetramethylgklycolide, $\beta$-butylrolactone, tetramethylglycolide, $\beta$-butyrolactone, gamma-butyrolactone, pivalolactone, and intermolecular cyclic esters of $\alpha$-hydroxybutyric acid, $\alpha$-hydroxyisobutyric acid, $\alpha$-hydroxyvaleric acid, $\alpha$-hydroxyisovaleric acid, $\alpha$-hydroxycaproic acid, $\alpha$-hydroxy-$\alpha$-ethylbutyric acid, $\alpha$-hydroxyisocaproic acid, $\alpha$-hydroxy-$\beta$-methylvaleric acid, $\alpha$-hydroxyheptanoic acid, $\alpha$-hydroxyoctanoic acid, $\alpha$-hydroxydecanoic acid, $\alpha$-hydroxymyristic acid, $\alpha$-hydroxystearic acid, $\alpha$-hydroxylignocenic acid, and $\alpha$-phenyllactic acid.

Methods of preparing poly(lactic acid) are well documented in the patent literature. The following patents, the teachings of which are hereby incorporated by reference, describe in detail suitable poly(lactic acids), their properties and their preparation: Dorough, U.S. Pat. No. 1,995,970; Schneider, U.S. Pat. No. 2,703,316; Salzberg, U.S. Pat. No. 2,758,987; Zeile, U.S. Pat. No. 2,951,828; Higgins, U.S. Pat. No. 2,676,945; Higgins, U.S. Pat. No. 2,683,136; Trehu, U.S. Pat. No. 3,531,561; British Patent Specification Nos. 755,447; 779,291; 825,335; 901,037; 932,382; 1,048,088; 1,123,445; West German Pat. Nos. 946,664; 975,191; 1,112,293; 1,152,258; 1,153,902; East German Pat. No. 14,548; French Pat. Nos. 1,425,333; 1,478,694; 1,512,182; Netherlands Pat. No. 99,836; Netherlands Patent Applications 6,605,197; 6,605,292; Japanese 17,675 (1966); 7,796 (1967); 2,948 (1968); 15,789 (1969).

Polyglycolic acids have recently been found to possess excellent biodegradable properties. Polyglycolic acid is the homopolymer of glycolic acid (hydroxyacetic acid). In the conversion of glycolic acid to polyglycolic acid, glycolic acid is initially reacted with itself to form the cyclic ester glycolide, which in the presence of heat and a catalyst, is converted to a high molecular weight linear-chain polymer. Polyglycolic acids and their properties are described in more detail in the following article, the teachings of which are hereby incorporated by reference: "Cyanamid Research Develops World's First Synthetic Absorbable Suture"; *Chemistry and Industry*, July 11, 1970, page 905.

The molecular weight of poly(lactic acids) and polyglycolic acid are closely related to both the exudation of agent and the biodegradation of the matrix. It has been found that high molecular weights, i.e., $\overline{M}w=90,000$ or higher result in polymer matrices which retain their structural integrity for longer periods of time; while lower molecular weights, i.e. $\overline{M}w=30,000$ or below, results in a shorter matrix life.

Crystallinity also affects the exudation and biodegradability rates. The polymer matrices having higher degrees of crystallinity have slower exudation rates and slower biodegradability. It is known, of course, that crystallinity has a marked effect on physical properties. See Flory, Paul J., *Principles of Polymer Chemistry*, 5th printing, 1966 at pages 49 et seq. It has also been reported in the literature that gaseous diffusion through polymeric membranes is slower, in general, for those polymers having higher degrees of crystallinity than for those with lower degrees of crystallinity. See Michaels, A. S. and Bixler, H. J., "Flow of Gases through Polyethylene and Rubbery Polymers", J. Poly Sci., vol. 50, pages 413-439 (1961).

A good amount of control over the release of agent can be obtained by choosing appropriate molecular weights and degrees of crystallinity of the polymer matrix. For example, if a relatively long release duration is desired, a high molecular weight polymer formed from a pure optical isomer of lactic acid can be used for the matrix; on the other hand, if a more rapid release rate is desirable over a short duration, a low molecular weight lactic acid copolymer having a lower degree of crystallinity can be synthesized for use as the polymer matrix. It is also known that release rate can be adjusted by varying the temperature or other conditions of matrix fabrication. Those skilled in the art will know or be able to determine by routine experimentation many suitable combinations of molecular weights, degrees of crystallinities of poly(lactic acids) or polyglycolic acid, and matrix fabrication parameters to accomplish a desired release rate and duration.

Using one or more of the above parameters, polymeric matrices can be designed which have a great variety of exudation rates and biodegradability. Matrices can be synthesized to have lives shorter than, equal to or longer than the period of effective agent delivery. For the shorter matrix lives, agent delivery will be accomplished by a combination of exudation and matrix biodegradation; for the longer matrix lives, agent delivery will be accomplished by a combustion of exudation and matrix biodegradation; for the longer matrix lives, agent delivery will be substantially dependent on only exudation. The degree of flexibility thus offered in designing anticancer agent dispensing system of this invention is of great significance.

The biodegradable polymeric materials described above have one or more anticancer agents incorporated in them to form the article of this invention. The term anticancer agent is used in this description in its broadest sense and covers any compound useful in controlling, limiting, and/or curing any of the known forms of cancer in mammals.

An example of anticancer agents are the drugs or combinations of drugs useful for treating leukemia such as the nitrogen mustard p-(di-2-chloroethyl) aminophenylbutyric acid. A derivative of nitrogen mustard which has proven particularly effective is cyclophosphamide which has the structural formula,

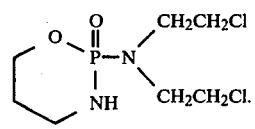

Another anticancer agent which has proven to be useful in cancer chemotherapy is doxorubicin, which can be represented by the structural formula,

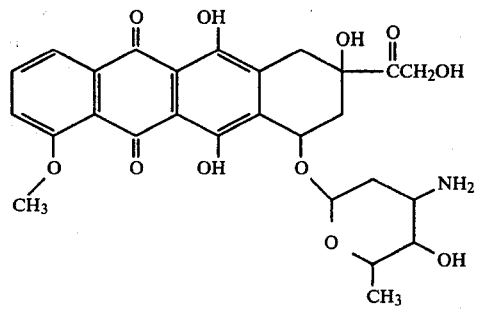

Still another suitable anticancer agent is the platinum compound cis-dichlorodiammine-platinum(II), which can be represented by the formula,

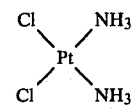

It is particularly preferred to use cis-dichlorodiammine-platinum(II) in combination with one or more additional anti-cancer agents. In fact, it has unexpectedly been found that cyclophosphamide acts not only as an anticancer agent, but also as a plasticizer for the composite when platinum compound and cyclophosphamide are dispersed in a poly(acetic acid) matrix. This dramatically increases the release rate of the platinum compound which otherwise is slow since it normally is quite insoluble in poly(lactic acid).

The above listing of anticancer agents is not intended to be comprehensive, but merely representative of the wide variety of such agents which can be used with this invention. Those skilled in the art will know or be able to determine by routine experimentation that many other specific anticancer agents are also suitable.

The amount of agent dispersed in the polymeric article will depend, of course, on many factors including the specific agent or agents, the length of time it is desired to dispense the agents, the total amount of agent to be dispensed in a specified time, the size of the device, and many other factors. In general, amounts ranging from about 0.5% to about 50% by weight of the polymeric material can be incorporated. Particularly good results can be obtained with from at least about 10% to about 20%.

The amount of agent to be dispensed in a specified time, will of course, depend on such factors as the particular cancer, the particular agent, the age of the patient, etc. In general, what will constitutes an "effective anticancer amount" will be known or easily ascertainable by those skilled in the art. Much of this type of data is published in the literature or easily determined by routine experimentation.

In addition to the control over delivery of agents which can be obtained through proper choice and design of the polymer matrix as discussed supra, the dosage administered by this dispenser can be controlled by the size and shape of the article, concentration of agent in the polymer, surface area, pore size, matching of the polymer and agent, nature of the surroundings, etc. This is a particular advantage where it is desirable to deliver a metered amount of the agent over a specified period of time.

Of course, substances in addition to the specific anticancer agents can also be incorporated into the polymeric material. For example, radioactive tracers such as carbon-14, nonradioactive tracers such as barium sulfate, carriers which would transport the agents through skin such as dimethylsulfoxide and dimethylsulfone, water-soluble excipients, etc. could be incorporated with certain agents for particular applications. The amount of auxiliary substances used will depend, of course, on the specific agent and polymer used to fabricate the article as well as the purpose for incorporating the auxiliary substances.

As has been described, the polymeric article dispenses the agents it contains by exuding them to the surface of the article. The mechanism of how the agent enters the body from the polymer surface is not critical and can be accomplished with a variety of techniques. For example, the article may be placed upon a person's body in contact with the skin so that the particular agent could be absorbed through the person's skin into the bloodstream. An alternative technique is to implant the device within the patient's body at a location where the surface layer of agent will be in contact with any of the various body fluids or tissue so that the agent could be dissolved and/or carried away by such body fluids or rubbed off and absorbed by the tissue. Subcutaneous implantation of a polymer matrix is an example. Intramuscular implantation is also contemplated. Still another technique would be to prepare the article for use in the patient's mouth so that the saliva would carry the agent into the body. In certain cases, it might be advantageous to insert the dispenser in other body cavities, such as the uterus or peritoneal cavity. Other techniques for getting the material from the surface of the article into the body will be readily apparent to the medical profession.

The dispensing articles described herein can be formed by pre-mixing the polymer, anticancer agents, plasticizers and any other auxiliary agents to be incorporated with the agents and then following conventional techniques to shape and set the article. For example, the polymer and agent can be mixed together in a suitable solvent until a homogeneous solution is formed. After driving off solvent, the residue can be molded, extruded, etc. to the desired shape. Another method of forming the dispenser might be to compact at elevated pressure a dry mixture of agent and polymer. Also, monomer and agent can be mixed with subsequent polymerization of the monomer.

Another method of forming the anticancer agent dispensers is to soak a previously shaped piece of polymeric material in a solution of agent to be incorporated, and subsequently drying the surface of the article. This technique must be distinguished, however, from simply dipping a polymeric article in a solution to coat the surface of the article with a substance. In the soaking technique of this invention, the conditions, i.e. solvent, polymer, temperature, etc., must be carefully chosen to insure that the active ingredient penetrates deeply into the polymer matrix instead of remaining only on the surface or penetrating a small distance below the surface as a coating does. One way to accomplish the desired deep penetration is to choose a solvent which causes the polymer to swell in the solution of agent. Some solvents cause swelling at room temperatures; others require elevated temperatures. Once the polymer has swollen, solvent and active ingredient can penetrate deeply into the polymer matrix. With rapid cooling, the polymer returns its non-swollen condition trapping solvent and active ingredient within it. If the solvent chosen is highly volatile, while the active ingredient is not, the solvent can be driven out of the article by continuous pumping, i.e. exposing the article to reduced pressures. Those skilled in the art will be able to select appropriate conditions for carrying out this technique.

Other methods for making the polymeric dispensing articles will be apparent to those skilled in the art.

An important feature of the dispenser, which results from the way it is prepared, is that there is a substantially intimate and uniform dispersion of agent throughout polymer. This is to be contrasted with a foraminous plastic matrix containing discrete solid particles of a drug only within the voids, such as described in U.S. Pat. Nos. 2,987,445 and 3,087,860. In these patented systems, drug release is predicated upon water or other liquids leaching the drug from the voids; in the dispenser of this invention, agent release is predicated upon exudation of the agent to the polymer surface.

Another important feature of the dispenser, which also results from the way it is prepared, is that the dispenser can be made to have "structural integrity". This means that the shaped dispenser will remain intact after prolonged exposure to body fluids. Although it is difficult to list all of the factors which contribute to the structural integrity, some include: substantial non-solubility and non-swellability in water or body fluids; relatively high tensile strengths; and good elongation at break and tensile modulus. Additionally, the polymeric matrices of this invention do not soften appreciably at temperatures as high as 100° C. as many of the prior art waxy binders do.

A test to establish structural integrity is as follows. The shaped drug carrier is immersed in distilled water at 37° C. for 7 days. After this period, weight loss of carrier and dimensional changes of carrier should be less than 10% of their original values. The polymeric matrices of this invention meet this test.

The shape of the dispenser will depend on its intended use. Any shape is within the scope of this invention. Some possible and preferred shapes are illustrated in FIG. III wherein (a) illustrates a film, (b) illustrates a piece of hollow tubing, and (c) illustrates various sized solid spheroids or particles which could be injected into a patient or orally ingested by the patient. Other shapes contemplated but not shown include solid "spaghetti-like" and "fiber-like" configurations and a mesh configuration which would be expected to minimize the possibility of a device subcutaneously implanted causing blood clotting. Another embodiment comprises a sphere formed from an outer coating of poly(lactic acid) with a solution of agent at the center.

The following Example serves to further illustrate the invention. All parts and percentages are by weight, unless otherwise specified.

EXAMPLE 1

Preparation of PLA/cis-Pta₂Cl₂/Tributyl Citrate Composites

A vacuum-dried sample of poly(lactic acid) (PLA) (4.225 g), prepared using the procedure reported in Woodland, J. H. R., Yolles, S., Blake, D. A., Helrich, M. and Meyer, F. J., *J. Med. Chem.*, 16, 897 (1973). This sample was dissolved in 25 ml of warm dichloromethane and, to the pale yellow solution, cooled to r.t., tributyl citrate (TBC) (0.325 g) was added dropwise while stirring. The solution had a viscosity similar to that of mineral oil. Cis-dichlorodiammine-platinum(II) (cis-Pta₂Cl₂) (1.950 g) was added slowly (two hrs.) while stirring. The mixture was transferred to a 500 ml ball mill jar about one-third filled with pebbles and rotated overnight. After separation from the pebbles, the fine suspension was evaporated to dryness and the dark yellow brittle film was broken up into small chips, vacuum-dried at 50° for 4 days, melt-pressed on a Carver laboratory press, model C, at 165°–175° C. under a total load of 3 metric tons for 10 secs. to produce films of uniform thickness in which no imperfection due to air or gas was observed. The films were ground in a grinder for 5 mins. and the resulting particles were screened by using USA standard testing sieves for 2 mins. Three fractions were collected which had average particle sizes of <110μ, 150–250μ, and 250–425μ.

EXAMPLE 2

Preparation of PLA/cis-Pta₂Cl₂/Cyclophosphamide Composites

In these composites, cyclophosphamide was used as an anticancer agent and as a plasticizer. A vacuum-dried sample of PLA (5.233 g) was dissolved in 25 ml of warm dichloromethane. To the yellow solution cooled to r.t. was added while stirring a solution of cyclophosphamide (1.409 g, taken from medical vials) in 45 ml of dichloromethane and then cis-Pta₂Cl₂ (1.294 g). The mixture was transferred to a 500 ml ball mill jar, one-third filled with pebbles, and rotated overnight. The mixture was worked up as described in Example 1 and two fractions of average sizes of 150–250μ and <110μ were collected.

EXAMPLE 3

Preparation of PLA/cis-Pta₂Cl₂/TBC/Cyclophosphamide/Doxorubicin Composites

Doxorubicin hydrochloride (D-HCl) was first converted to the free base by bubbling gaseous ammonia slowly through a capillary pipet into a stirred suspension of D-HCl (0.050 g) in 15 ml of an 8:1 mixture of chloroform and methanol. The bubbling of ammonia was continued until the mixture was red-orange. After the ammonium chloride settled by centrifugation, the supernatant liquid was filtered and the filtrate after dilution with 150 ml of the above solvent mixture was heated at 60° for one hour to give a solution of 0.037 g of free base of Doxorubicin in 100 ml of solvent. PLA (0.72 g), tributyl citrate (TBC) (0.14 g), cis-Pta₂Cl₂ (0.16 g) and cyclophosphamide (0.18 g) were added while stirring. The mixture was concentrated to dryness and worked up as described in Example 1 to yield two samples of average particle sizes of 250–425μ and 150–250μ.

EXAMPLE 4

Preparation of PLA/cis-Pta₂Cl₂/Cyclophosphamide/Doxorubicin Composites

To a dark orange solution of Doxorubicin (0.036 g), prepared from Doxorubicin hydrochloride as described in the previous experiment, in chloroform (100 ml) were added while stirring at 50° PLA (4.048 g), cis-Pta₂Cl₂ (0.495 g) and cyclophosphamide (0.381 g in 40 ml dichloromethane). The mixture was transferred to a 500 ml ball mill jar about one-third filled with pebbles, rotated overnight and worked up as reported in Example 1 to give two samples of average particle sizes of 250–425μ and 150–250μ.

A summary of the composites formed in Examples 1–4 is presented below in Table I.

TABLE I

| Composite | % cis-Pta₂Cl₂ | Particle Size, μ |
|---|---|---|
| PLA/cis-Pta₂Cl₂/TBC | 30 | 150–250 |
|  | 30 | <100 |
|  | 30 | 250–425 |
| PLA/cis-Pta₂Cl₂/cyclophosphamide | 16.3 | 150–250 |
|  | 16.3 | <110 |
| PLA/cis-Pta₂Cl₂/Cyclophosphamide/Doxorubicin | 13.3 | 250–425 |
|  | 13.3 | 150–250 |
| PLA/cis-Pta₂Cl₂/Cyclophosphamide/Doxorubicin | 10.0 | 250–425 |
|  | 10.0 | 150–250 |

EXAMPLE 5

IN VITRO RELEASE

The release rates of the platinum compound from composites with PLA were determined by dialyzing 0.874 g of a composite containing 30% of cis-Pta₂Cl₂ and having a particle size of 250–425μ with Ringer's solution. The dialysis cell consisted of two Plexiglass blocks 8×12×2 cm with hemispherical chambers separated by a lambskin membrane, which was kept suspended in distilled water for 5 days to remove surface adjuvants, the oily water being replaced each day with fresh water.

The following procedure was used: The assembled dialysis cell was placed on a magnetic stirrer and the inlet needle in the lower half of the cell was connected to a pump (peristaltic) which delivered about 10 ml/hour of Ringer's solution), being careful to remove all air bubbles from below the surface of the membrane. (This insures contact between dialyzing fluid and the whole membrane surface.)

Dialyzing fluid (1–2 ml), which remained static through the experiment, was placed in the upper half of the cell. The composite sample was added through a 5 mm hole in the top of the cell and, while stirring, the upper chamber was filled to capacity by means of a fine tipped eyedropper (Pasteur dropper). Samples of dialysis effluent were collected daily for 92 days.

The samples were analyzed the same day of collection for Pt by atomic absorption spectrometry, using a Perkin-Elmer Model 337 and the most sensitive line for Pt (3064.7 Å) being used.

For material balance calculation, the composite left in the cell at the end of the experiment and the composite adherent to the membrane was transferred into a beaker with warm distilled water. The suspension was stirred for 30 mins. and the water allowed to evaporate at 50° overnight. To the residue was added dichloromethane (250 ml) and the mixture stirred overnight at r.t. to dissolve PLA and TBC. The insoluble material was collected by filtration, washed with a little cold water, dried under vacuum at 60° C. for 3 hrs. to give 0.114 g of yellow-green platinum compound.

The in vitro release of cis-$Pta_2Cl_2$ from PLA composites, determined by the membrane dialysis technique described above, is shown in FIGS. 1 and 2. The average daily delivery of platinum compound was 1.42 mg and the total amount of platinum compound released during the 92 day test was 0.131 g or 50% of the amount of $Pta_2Cl_2$ present in the composites. This total amount of Pt delivered is in agreement with the material balance calculation previously mentioned.

From the data of FIG. 2, it is possible to conclude that the process is essentially first order from Days 0–62 and essentially zero order from Days 63–92.

EXAMPLE 6

IN VIVO RELEASE

These experiments were performed in the standard assay of the Ascites Sarcoma 180 in the ICR mice. There were six mice in each cage, with two cages for the negative controls, two cages for the positive controls and one cage for each dose level of drug tested. Tumor cell injections were performed on Day 0 and drug injection Day 1, both given intraperitoneally. Suspensions in carboxymethyl cellulose of the amounts of drugs, as listed in Table II, and saline as a carrier were used.

The results of the in vivo tests performed on mice with the various types of composites prepared can be seen from Table II. The time of evaluation varied from 37 to 47 days. These tests confirm the feasibility of a time-release system for delivering anticancer agents. Some composites were significantly better than the positive control (7 mg/Kg single injection of cis-dichlorodiamine-platinum(II)). The improvement in the life span compared to the positive control is substantial and the number of cures is a marked improvement over the single injection method. Furthermore, the toxicity of the drug, $Pta_2Cl_2$, has certainly been decreased by this slow release system. For example, for composites of PLA/cis-$Pta_2Cl_2$/cyclo, it was possible to use dose levels of upwards of 32 mg/Kg mouse; straight cis-$Pta_2Cl_2$ is toxic at 8 mg/Kg mouse. In addition, with composites of PLA/cis-$Pta_2Cl_2$/Doxorubicin/Cyclophosphamide, 64 mg/Kg could be tolerated.

TABLE II

| Compound | Dose mg $Pta_2Cl_2$/ Kg mouse | Average Day of Death | % Increased Life Span | No. of Cures |
|---|---|---|---|---|
| Day of Evaluation - 37 | | | | |
| Negative Control | — | 18.4 | — | — |
| Positive Control | 7 | 24.8 | 34.8 | 1 |
| CMC-7LF | 37.5 | 14.3 | −22.3 | — |
| PLA/cis-$Pta_2Cl_2$/TBC (150–250μ) | 8 | 17.2 | −6.5 | — |
|  | 16 | 20.8 | 13.0 | — |
| PLA/cis-$Pta_2Cl_2$/TBC (<100μ) | 8 | 27.7 | 50.5 | 2 |
|  | 16 | 31.5 | 71.2 | 3 |
| PLA/cis-$Pta_2Cl_2$/cyclophosphamide (150–250μ) | 8 | 24.5 | 33.2 | — |
|  | 16 | 22.3 | 21.2 | — |
| PLA/cis-$Pta_2Cl_2$/cyclophosphamide (<110μ) | 8 | 23.5 | 27.7 | 1 |
|  | 16 | 29.7 | 61.4 | 2 |
| Day of Evaluation - 40 | | | | |
| Negative Control | — | 20 | — | — |
| Positive Control | 7 | 30 | 50.5 | 1 |
| PLA/cis-$Pta_2Cl_2$/TBC/ Cyclophosphamide/Doxorubicin (250–425μ) | 8 | 28.3 | 41.5 | 1 |
| PLA/cis-$Pta_2Cl_2$/TBC/ Cyclophosphamide/Doxorubicin (150–250μ) | 8 | 27.7 | 38.5 | — |
| Day of Evaluation - 47 | | | | |
| Negative Control | — | 23.4 | — | — |
| Positive Control | 7 | 27.9 | 19.2 | 1 |
| PLA/cis-$Pta_2Cl_2$/TBC (<100μ) | 32 | 22.3 | −4.7 | 1 |
|  | 64 | 11.0 | −53.0 | 1 |
| PLA/cis-$Pta_2Cl_2$/Cyclophosphamide (<100μ) | 32 | 37.8 | 61.5 | 3 |
|  | 64 | 2.7 | −88.5 | — |
| PLA/cis-$Pta_2Cl_2$/TBC/Cyclophosphamide/ Doxorubicin (150–250μ) | 32 | 33.3 | 42.3 | 2 |
|  | 64 | 27.7 | 18.4 | 2 |
| PLA/cis-$Pta_2Cl_2$/Cyclophosphamide/ Doxorubicin (250–425μ) | 32 | 31.5 | 34.6 | 1 |
|  | 64 | 31.0 | 32.5 | 2 |
| PLA/cis-$Pta_2Cl_2$/Cyclophosphamide/ Doxorubicin (150–250μ) | 32 | 36.7 | 56.8 | 3 |
|  | 64 | 27.7 | 18.4 | 3 |

Those skilled in the art will recognize many equivalents to the specific elements, components, materials, steps, etc. described as preferred embodiments herein. Such equivalents are intended to be covered by the following claims:

What is claimed is:

1. An implant drug dispensing device article for prolonged administration upon implantation of an anticancer agent which comprises, a solid shaped article formed from a combination of
    (a) a biodegradable polymer selected from poly(lactic acid) or polyglycolic acid, and, substantially uniformly and intimately dispersed throughout portions of the article,
    (b) cis-dichlorodiammine-platinum (II), and
    (c) doxorubicin or cyclophosphamide each being present in administrable doseage being much larger than those normally toxic, to lower than are normally infused by injection, and having an average particle size of from 150 to 425 microns.

2. The article of claim 1 wherein the biodegradable polymer is poly(lactic acid).

3. A method of treating cancer in a mammal susceptible to treatment with cis-dichlorodiammine-platinum (II) comprising implanting an article according to claim 1 into the body of said mammal.

* * * * *